United States Patent
Towler et al.

(10) Patent No.: US 7,973,209 B1
(45) Date of Patent: *Jul. 5, 2011

(54) FRACTIONATION RECOVERY PROCESSING OF LIGHT OLEFINS FREE OF CARBON DIOXIDE

(75) Inventors: Gavin P. Towler, Inverness, IL (US); John P. Brady, Algonquin, IL (US); William J. Lechnick, Glen Ellyn, IL (US); Michael A. Schultz, Chicago, IL (US)

(73) Assignee: UOP LLC, Des Plaines, IL (US)

( * ) Notice: Subject to any disclaimer, the term of this patent is extended or adjusted under 35 U.S.C. 154(b) by 903 days.

This patent is subject to a terminal disclaimer.

(21) Appl. No.: 11/541,310

(22) Filed: Sep. 28, 2006

(51) Int. Cl.
*C10G 7/02* (2006.01)
*B01D 3/10* (2006.01)
*C07C 7/00* (2006.01)

(52) U.S. Cl. ........ 585/802; 585/644; 585/648; 585/650; 585/651; 585/653; 585/803; 585/809; 585/843; 208/114; 208/118; 208/120.1; 208/347; 208/351; 208/354; 62/622; 62/625; 62/632; 62/935

(58) Field of Classification Search .......... 585/644, 585/648, 650, 651, 653, 802, 803, 809, 843, 585/844; 208/114, 118, 120.1, 347, 351, 208/354; 62/622, 625, 632, 935
See application file for complete search history.

(56) References Cited

U.S. PATENT DOCUMENTS

| | | | |
|---|---|---|---|
| 2,813,920 A | 11/1957 | Cobb, Jr. | |
| 2,863,527 A | 12/1958 | Herbert et al. | |
| 3,409,693 A | 11/1968 | McHarg | |
| 3,552,924 A | 1/1971 | Hepp | |
| 3,702,886 A | 11/1972 | Argauer et al. | |
| 3,829,521 A * | 8/1974 | Green ........................ | 95/161 |
| 4,003,822 A | 1/1977 | Jo | |
| 4,072,604 A | 2/1978 | Ward | |
| 4,479,812 A | 10/1984 | Hsia et al. | |
| 4,894,141 A | 1/1990 | Busch et al. | |
| 5,015,364 A | 5/1991 | Harandi | |
| 5,110,446 A | 5/1992 | Harandi et al. | |
| 5,360,533 A | 11/1994 | Tagamolila et al. | |
| 5,447,621 A | 9/1995 | Hunter | |
| 5,584,985 A | 12/1996 | Lomas | |
| 5,820,837 A | 10/1998 | Marjanovich et al. | |
| 5,858,206 A | 1/1999 | Castillo | |
| 5,859,304 A * | 1/1999 | Barchas et al. .............. | 585/809 |
| 6,110,356 A | 8/2000 | Hedrick et al. | |
| 6,139,605 A | 10/2000 | Carnell et al. | |
| 6,464,858 B1 | 10/2002 | Brown et al. | |

(Continued)

FOREIGN PATENT DOCUMENTS
EP 1 637 577 A2 3/2006

OTHER PUBLICATIONS

U.S. Appl. No. 11/540,110, filed Sep. 28, 2006, Schultz.

(Continued)

*Primary Examiner* — Prem C Singh
(74) *Attorney, Agent, or Firm* — James C Paschall (57) ABSTRACT

Processing schemes and arrangements for the catalytic cracking of a heavy hydrocarbon feedstock and obtaining light olefins substantially free of carbon dioxide via amine treatment and employing fractionation processing are provided.

19 Claims, 2 Drawing Sheets

U.S. PATENT DOCUMENTS

| | | |
|---|---|---|
| 6,538,169 B1 | 3/2003 | Pittman et al. |
| 6,540,907 B1 | 4/2003 | Towler et al. |
| 6,576,805 B2 * | 6/2003 | Keady et al. .................. 585/802 |
| 6,726,835 B2 | 4/2004 | Towler et al. |
| 6,838,587 B2 | 1/2005 | Lattner et al. |
| 6,843,906 B1 | 1/2005 | Eng |
| 6,927,314 B1 | 8/2005 | Schultz et al. |
| 6,946,068 B2 | 9/2005 | Groten |
| 7,074,971 B2 | 7/2006 | Van Egmond et al. |
| 7,312,370 B2 | 12/2007 | Pittman et al. |

OTHER PUBLICATIONS

U.S. Appl. No. 11/540,793, filed Sep. 28, 2006, Schultz.
U.S. Appl. No. 11/541,218, filed Sep. 28, 2006, Wegerer.
U.S. Appl. No. 11/540,088, filed Sep. 28, 2006, Schultz.
U.S. Appl. No. 11/541,200, filed Sep. 28, 2006, Schultz.

* cited by examiner

FRACTIONATION RECOVERY PROCESSING OF LIGHT OLEFINS FREE OF CARBON DIOXIDE

BACKGROUND OF THE INVENTION

This invention relates generally to hydrocarbon processing and, more particularly, to the processing of hydrocarbon-containing materials having a high light olefin content, such as produced or formed in or by the cracking of a heavy hydrocarbon feedstock.

Light olefins serve as feed materials for the production of numerous chemicals. Light olefins have traditionally been produced through the processes of steam or catalytic cracking of hydrocarbons such as derived from petroleum sources. Fluidized catalytic cracking (FCC) of heavy hydrocarbon streams is commonly carried out by contacting a starting material whether it be vacuum gas oil, reduced crude, or another source of relatively high boiling hydrocarbons with a catalyst such as composed of finely divided or particulate solid material. The catalyst is transported in a fluid-like manner by transmitting a gas or vapor through the catalyst at sufficient velocity to produce a desired regime of fluid transport. Contact of the oil with the fluidized material catalyzes the cracking reaction.

The cracking reaction typically deposits coke on the catalyst. Catalyst exiting the reaction zone is commonly referred to as being "spent", i.e., partially deactivated by the deposition of coke upon the catalyst. Coke is comprised of hydrogen and carbon and can include, in trace quantities, other materials such as sulfur and metals such that may enter the process with the starting material. The presence of coke interferes with the catalytic activity of the spent catalyst. It is believed that the coke blocks acid sites on the catalyst surface where the cracking reactions take place. Spent catalyst is traditionally transferred to a stripper that removes adsorbed hydrocarbons and gases from catalyst and then to a regenerator for the purpose of removing the coke by oxidation with an oxygen-containing gas. An inventory of catalyst having a reduced coke content, relative to the spent catalyst in the stripper, hereinafter referred to as regenerated catalyst, is collected for return to the reaction zone. Oxidizing the coke from the catalyst surface releases a large amount of heat, a portion of which escapes the regenerator with gaseous products of coke oxidation generally referred to as flue gas. The balance of the heat leaves the regenerator with the regenerated catalyst. The fluidized catalyst is continuously circulated between the reaction zone and the regeneration zone. The fluidized catalyst, as well as providing a catalytic function, serves as a vehicle for the transfer of heat from zone to zone. FCC processing is more fully described in U.S. Pat. No. 5,360,533 to Tagamolila et al., U.S. Pat. No. 5,584,985 to Lomas, U.S. Pat. No. 5,858, 206 to Castillo and U.S. Pat. No. 6,843,906 B1 to Eng, the contents of each of these patents are hereby incorporated herein by reference. Specific details of the various contact zones, regeneration zones, and stripping zones along with arrangements for conveying the catalyst between the various zones are well known to those skilled in the art.

The FCC reactor serves to crack gas oil or heavier feeds into a broad range of products. Cracked vapors from an FCC unit enter a separation zone, typically in the form of a main column, that provides a gas stream, a gasoline cut, light cycle oil (LCO) and clarified oil (CO) which includes heavy cycle oil (HCO) components. The gas stream may include dry gas, i.e., hydrogen and $C_1$ and $C_2$ hydrocarbons, and liquefied petroleum gas ("LPG"), i.e., $C_3$ and $C_4$ hydrocarbons, also sometimes commonly referred to as wet gas.

As a result or through such hydrocarbon cracking processing, byproduct species such as $CO_2$, $H_2S$ and other sulfur compounds may form or otherwise be present in the FCC effluent in undesirably high relative amounts. In the past, amine units have been used to separate species such as $CO_2$ from hydrocarbon stream materials. In typical amine systems, an amine solvent such as methyl diethanol amine [MDEA] is used to absorb or otherwise separate $CO_2$ from hydrocarbon stream materials. A stripper is typically subsequently used to strip the absorbed $CO_2$ from the amine solvent, permitting the reuse of the stripped amine solvent.

In view of an increasing need and demand for light olefins such as ethylene and propylene for various petrochemical uses such as for the production of polyethylene, polypropylene and the like as well as the desire to produce relatively less of heavier olefins such as butylenes and pentenes which are generally less desirable as gasoline blending components due to environmental considerations, it may be desired to practice the cracking reaction processing of heavy hydrocarbon feedstock to increase the relative amount of light olefins in the resulting product slate.

Research efforts have led to the development of an FCC process that produces or results in greater relative yields of light olefins, i.e., ethylene and propylene. Such processing is more fully described in U.S. Pat. No. 6,538,169 B1 to Pittman et al., the contents of which are hereby fully incorporated herein by reference. As disclosed therein, a hydrocarbon feed stream can desirably be contacted with a blended catalyst comprising regenerated catalyst and coked catalyst. The catalyst has a composition including a first component and a second component. The second component comprises a zeolite with no greater than medium pore size wherein the zeolite comprises at least 1 wt. % of the catalyst composition. The contacting occurs in a riser to crack hydrocarbons in the feed stream and obtain a cracked stream containing hydrocarbon products including light olefins and coked catalyst. The cracked stream is passed out of an end of the riser such that the hydrocarbon feed stream is in contact with the blended catalyst in the riser for less than or equal to 2 seconds on average.

As with conventional FCC processing, byproduct species such as $CO_2$, $H_2S$ and other sulfur compounds may form or otherwise be present in the resulting effluent in undesirably high relative amounts. However, whereas conventional FCC processing effluent streams typically have little if any olefin content, the such modified hydrocarbon processing desirably produces or results in an effluent stream having a significantly large olefin content. With standard amine system treatment of such large olefin content effluent streams, some of the olefin material is typically co-absorbed with the $CO_2$ in or by the amine solvent. Such co-absorption of olefin material undesirably reduces the amounts of light olefins available for recovery from such processing.

Moreover, in conventional amine treatment processing, the amine solvent containing the absorbed $CO_2$ is typically subjected to further processing such as through a stripper wherein the absorbed $CO_2$ can desirably be separated from the amine solvent and the amine solvent can be recycled and reused for amine treatment of a selected carbon dioxide-containing stream. Unfortunately, during such subsequent stripper processing of the amine solvent, the presence of such olefin materials can lead to polymerization. Such polymerization can lead to degradation of the amine solvent and require expensive off-site reclamation processing.

Thus, there is a need and a demand for processing and arrangements for increased effectiveness for the separation and removal of carbon dioxide from high olefin content process streams.

More particularly, there is a need and a demand for improved amine treatment processing arrangements and processing schemes of such high olefin content process streams such as for the effective separation and removal of carbon dioxide therefrom while desirably permitting increased or improved olefin recovery.

SUMMARY OF THE INVENTION

A general object of the invention is to provide an improved process and system for catalytic cracking a heavy hydrocarbon feedstock and obtaining light olefins substantially free of carbon dioxide.

A more specific objective of the invention is to overcome one or more of the problems described above.

The general object of the invention can be attained, at least in part, through a specified process such as involves contacting a heavy hydrocarbon feedstock with a hydrocarbon cracking catalyst in a fluidized reactor zone to produce a hydrocarbon effluent comprising a range of hydrocarbon products, including light olefins, and a quantity of carbon dioxide. The hydrocarbon effluent is subsequently separated to form at least one separator liquid stream and a separator vapor stream. The at least one separator liquid stream comprises $C_4+$ hydrocarbons substantially free of carbon dioxide. The separator vapor stream comprises $C_4-$ hydrocarbons and at least a portion of the quantity of carbon dioxide. The separator vapor stream is treated in an amine treatment section with an amine absorption solvent at treatment conditions effective to absorb a significant portion of the carbon dioxide from the contacted portion of the absorption zone effluent stream and to form a treated stream comprising $C_4-$ hydrocarbons substantially free of carbon dioxide. At least a portion of the treated stream comprising $C_4-$ hydrocarbons substantially free of carbon dioxide is subsequently fractionated to at least form a first light olefin product stream comprising ethylene substantially free of carbon dioxide and a second light olefin products stream comprising propylene substantially free of carbon dioxide.

The prior art generally fails to provide processing schemes and arrangements for obtaining light olefins substantially free of carbon dioxide via the catalytic cracking of a heavy hydrocarbon feedstock. More particularly, the prior art generally fails to provide such processing schemes and arrangements that advantageously utilize fractionation processing of hydrocarbon effluent products to produce or otherwise form process streams containing specifically desired ranges of hydrocarbons.

A process for catalytic cracking a heavy hydrocarbon feedstock and obtaining light olefins substantially free of carbon dioxide, in accordance with another embodiment involves contacting a heavy hydrocarbon feedstock with a regenerated catalyst in a fluidized reactor zone at hydrocarbon cracking reaction conditions to produce a hydrocarbon effluent stream comprising a range of hydrocarbon products including light olefins and a quantity of carbon dioxide. The catalyst desirably has a catalyst composition including a first component comprising a large pore molecular sieve and a second component comprising a zeolite with no greater than medium pore size, said zeolite with no greater than medium pore size comprising at least 1.0 wt. % of the catalyst composition. The hydrocarbon effluent is subsequently separated in a hydrocarbon separation section to form at least one separator liquid stream and a separator high pressure vapor stream. The at least one separator liquid stream comprises $C_4+$ hydrocarbons substantially free of carbon dioxide. The separator high pressure vapor stream comprises $C_4-$ hydrocarbons and at least a portion of the quantity of carbon dioxide. At least a portion of the separator high pressure vapor stream is contacted in an absorber zone with an amine absorption solvent and at contact conditions effective to absorb a significant portion of the carbon dioxide from the contacted portion of the separator high pressure vapor stream and to form a hydrocarbon-containing process stream substantially free of carbon dioxide and a carbon dioxide-rich amine absorption solvent-containing process stream. At least a portion of the carbon dioxide-rich amine absorption solvent-containing process stream is processed in a first stripping zone at first stripping conditions effective to strip at least a portion of hydrocarbons remaining in the carbon dioxide-rich amine absorption solvent-containing process stream to form a first process stream comprising stripped hydrocarbons and a second process stream comprising carbon dioxide and amine absorption solvent. At least a portion of the second process stream is processed in a second stripping zone at second stripping conditions effective to strip at least a portion of the carbon dioxide from the second process stream to form a carbon dioxide purge stream and an amine stream. At least a portion of the first process stream comprising stripped hydrocarbons is fractionated to at least form a first light olefin product stream comprising ethylene substantially free of carbon dioxide and a second light olefin products stream comprising propylene substantially free of carbon dioxide. In accordance with one embodiment, the regenerated catalyst can be a part of a blended catalyst that also includes coked catalyst.

A system for catalytically cracking a heavy hydrocarbon feedstock to obtain light olefins is also provided. In accordance with one preferred embodiment, such as system includes a fluidized reactor zone wherein the heavy hydrocarbon feedstock contacts a blended catalyst comprising regenerated catalyst and coked catalyst at hydrocarbon cracking reaction conditions to produce a cracked stream containing hydrocarbon products including light olefins and a quantity of carbon dioxide. A separator section is provided to separate the cracked stream to form a high pressure separator liquid stream comprising $C_4+$ hydrocarbons and a high pressure separator vapor stream comprising $C_4-$ hydrocarbons and at least a portion of the quantity of carbon dioxide. The system further includes an amine treatment section to treat the high pressure separator vapor stream by contacting at least a portion of the high pressure separator vapor stream with an amine absorption fluid at contact conditions effective to absorb a significant portion of the carbon dioxide from the contacted portion of the high pressure separator vapor stream and to form a hydrocarbon-containing, light olefin-rich process stream substantially free of carbon dioxide and a carbon dioxide-rich amine absorption fluid-containing process stream. A fractionation zone is provided to separate the light olefin-rich process stream substantially free of carbon dioxide and a carbon dioxide-rich amine absorption fluid-containing process stream to at least form a first light olefin product stream comprising ethylene substantially free of carbon dioxide and a second light olefin products stream comprising propylene substantially free of carbon dioxide. In accordance with one embodiment the catalyst may desirably be in the form of a blended catalyst including regenerated catalyst and coked catalyst.

As used herein, references to "light olefins" are to be understood to generally refer to $C_2$ and $C_3$ olefins, i.e., ethylene and propylene, alone or in combination.

References to a process stream as "ethylene-rich" are to be understood to generally refer to such process streams as generally contain at least 20 percent ethylene and, in accordance with at least certain preferred embodiments alternatively contain at least 25 percent ethylene, at least 30 percent ethylene, at least 35 percent ethylene, at least 40 percent ethylene or about 40 to about 60 percent ethylene.

References to light olefin materials or appropriate process streams as being "substantially free of carbon dioxide" are to be understood to generally refer to such light olefin materials or process streams as desirably generally containing less than about 100 ppm of carbon dioxide, preferably containing less than about 10 ppm of carbon dioxide and, more preferably, desirably containing less than about 1 ppm of carbon dioxide.

References to "$C_x$ hydrocarbon" are to be understood to refer to hydrocarbon molecules having the number of carbon atoms represented by the subscript "x".

Similarly, the term "$C_x$-containing stream" refers to a stream that contains $C_x$ hydrocarbon. The term "$C_x$+ hydrocarbons" refers to hydrocarbon molecules having the number of carbon atoms represented by the subscript "x" or greater. For example, "$C_4$+ hydrocarbons" include $C_4$, $C_5$ and higher carbon number hydrocarbons. The term "$C_x$− hydrocarbons" refers to hydrocarbon molecules having the number of carbon atoms represented by the subscript "x" or fewer. For example, "$C_4$− hydrocarbons" include $C_4$, $C_3$ and lower carbon number hydrocarbons.

Other objects and advantages will be apparent to those skilled in the art from the following detailed description taken in conjunction with the appended claims and drawings.

Those skilled in the art and guided by the teachings herein provided will recognize and appreciate that the illustrated system or process flow diagrams have been simplified by the elimination of various usual or customary pieces of process equipment including some heat exchangers, process control systems, pumps, fractionation systems, and the like. It may also be discerned that the process flow depicted in the figures may be modified in many aspects without departing from the basic overall concept of the invention.

DETAILED DESCRIPTION

A stream rich in ethylene and containing carbon dioxide can be processed to effectively and efficiently to remove carbon dioxide therefrom. Additionally, a heavy hydrocarbon feedstock can be effectively and efficiently processed via hydrocarbon cracking processing to obtain light olefins substantially free of carbon dioxide.

Figure 1:
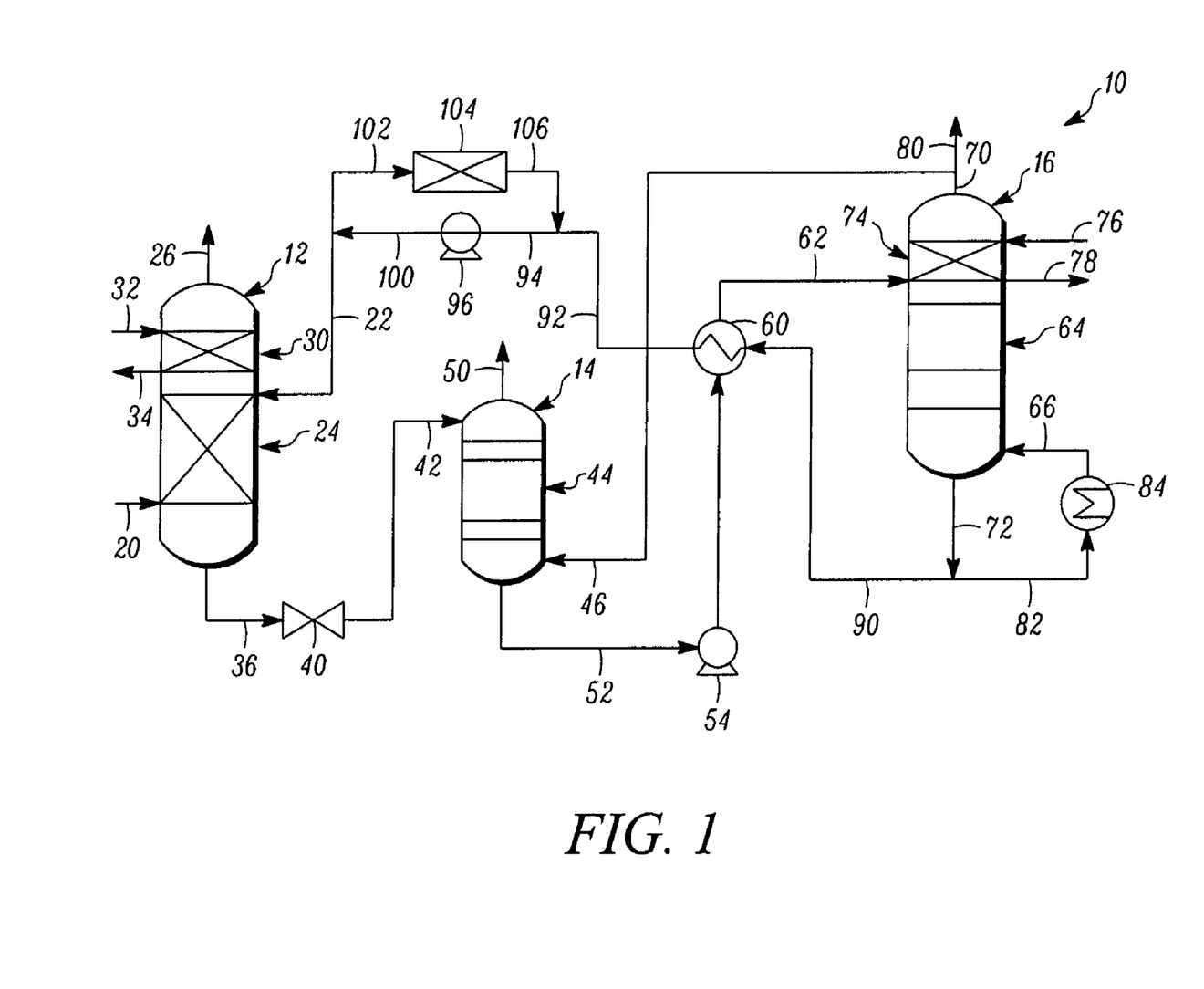
FIG. 1 is a simplified schematic diagram of an amine treatment section for the processing of a hydrocarbon process stream in accordance with one preferred embodiment.

FIG. 1 schematically illustrates an amine treatment section, generally designated by the reference numeral 10, for the processing of a hydrocarbon process stream for the removal of carbon dioxide therefrom, in accordance with one preferred embodiment. As described in greater detail below, the amine treatment section 10 includes the following major components or elements: an absorber zone 12, a first stripping zone 14 and a second stripping zone 16.

More particularly, a suitable ethylene-rich hydrocarbon and carbon dioxide-containing stream such as derived from hydrocarbon cracking processing of a heavy hydrocarbon feedstock, as described in greater detail below, is suitably introduced via a line 20 into the absorber zone 12.

As described above, ethylene-rich hydrocarbon and carbon dioxide-containing streams as used herein generally refer to carbon dioxide-containing hydrocarbon streams that typically contain somewhere in the range of about 0.5 mol. % to about 2.5 mol % carbon dioxide and also generally contain at least 20 percent ethylene and, in accordance with at least certain preferred embodiments alternatively contain at least 25 percent ethylene, at least 30 percent ethylene, at least 35 percent ethylene, at least 40 percent ethylene or about 40 to about 60 percent ethylene. In general, such a stream of material to be treated will typically be at a temperature of about 100-120° F. (38-49° C.) and a pressure in the range of about 2750-3450 kPag (about 400-500 psig).

An absorption solvent to affect desired $CO_2$ absorption is introduced into the absorption zone 12 via a line 22. Suitable absorption solvents for use in the practice of the invention include various such materials such as known in the art to effect removal of $CO_2$ and $H_2S$. Those skilled in the art and guided by the teachings herein provided will appreciate, for example, that aqueous solutions of various amine absorption solvents such as known in the art to effect removal of $CO_2$ and $H_2S$ can be used in the practice of the invention and thus the broader practice of the invention is not necessarily limited by or to practice with particular or specific absorption solvents. Suitable absorption solvents for use in the practice of the invention include tertiary amines such as methyl diethanol amine (MDEA), secondary amines such as diethanol amine (DEA) and diisopropanol amine (DIPA) and primary amines such as monoethanol amine (MEA), for example.

As will be appreciated by those skilled in the art and guided by the teachings herein provided, suitable absorption zones for use in the practice of the invention may desirably be in the form of a column and contains or includes an active absorber section or portion 24 such as includes trays, packing or other column internals such as may be desired to facilitate or otherwise help effect the desired absorption action. A suitable such amine system absorber, in accordance with one preferred embodiment, desirably operates at a pressure in the range of about 1720 kPag to about 3450 kPag (about 250 psig to about 500 psig), more preferably in a range of about 3100 kPag to about 3450 kPag (about 450 psig to about 500 psig), and with a bottoms temperature in the range of about 40° to about 80° C.

As shown, the point of introduction into the absorption zone 12 of the line 20 containing the stream of material to be treated, i.e., the ethylene-rich hydrocarbon and carbon dioxide-containing stream, may desirably be situated below the active absorber section 24 and the point of introduction into the absorption zone 12 of the line 22 containing the stream of the absorption solvent may desirably be situated above the active absorber section 24, such that the absorption solvent and the material to be treated within the absorption zone are in at least a general countercurrent flow arrangement. Moreover, such placement of the points of introduction of the stream of material to be treated and the absorption solvent, respectively, can desirably maximize the effect of any column internals and the effective contact time and residence time of the stream materials within the active absorber section 24.

A stream of treated gas is withdrawn from the absorption zone 20 via an overhead line 26. Prior to exiting the absorption zone 20, the gas is passed through a wash zone 30 where a wash material such as water is introduced through a line 32 to contact the treated gas and to desirably remove entrained absorption solvent that may have remained therewith. The used wash material containing such removed absorbent material is withdrawn from the absorption zone via a line 34 and can desirably be sent for absorption solvent recovery processing (not shown), as is known in the art.

It is to be understood that the treated gas in the overhead line 26 or one or more selected portions thereof may, if desired, be subjected to additional processing (not shown) such as via a caustic treatment step to ensure that the $CO_2$ and $H_2S$ have been suitably removed to the level required for desired light olefin product specifications.

A carbon dioxide-rich absorption solvent-containing process stream is withdrawn from the absorption zone 12 via a line 36. The carbon dioxide-rich absorption solvent-containing process stream or at least a portion thereof is passed via a valve 40 and a line 42 to the first stripping zone 14.

As will be appreciated by those skilled in the art and guided by the teachings herein provided, suitable first stripping zones for use in the practice of the invention may desirably be in the form of a column and contains or includes an active stripping section or portion 44 such as includes a selected number of trays or other stripping column internals such as may be desired to facilitate or otherwise help effect the desired stripping action. As shown, the point of introduction into the first stripping zone 14 of the line 42 containing the stream of carbon dioxide-rich absorption solvent may desirably be situated above the active stripping section 44 and the point of introduction into the first stripping zone 14 of a line 46 containing a stream of a selected stripping fluid may desirably be situated below the active stripping section 44, such that the stripping fluid and the material to be treated within the first stripping zone 14 are in at least a general countercurrent flow arrangement. Moreover, such placement of the points of introduction of the stream of material to be treated and the stripping fluid, respectively, can desirably maximize the effect of any column internals and the effective contact time and residence time of the stream materials within the first stripping zone active stripping section 44.

Thus, whereas conventional amine treatment systems such as used in the treatment of conventional FCC effluent streams may simply employ a flash column, the incorporation and use of a stripping zone such as the above-described first stripping zone 14 helps ensure the desired separation of present hydrocarbons including ethylene and propylene such as may otherwise be more strongly physisorbed than non-olefinic hydrocarbons.

In accordance with one preferred embodiment, the first stripping zone 14 desirably includes a stripper column such as having typically less than 15 ideal stages and generally no more than about 8-12 ideal stages.

The first stripping zone 14 is desirably operated in a manner, including first stripping conditions, effective to strip at least a portion of hydrocarbons remaining in the carbon dioxide-rich absorption solvent-containing process stream therefrom and to form a first process stream containing stripped hydrocarbons and a second process stream containing carbon dioxide and absorption solvent. Suitable such stripping conditions generally include: an operating pressure such as in the range of about 34 kPag to about 173 kPag (about 5 psig to about 25 psig) or, in accordance with one preferred embodiment in the range of about 34 kPag to about 69 kPag (about 5 psig to about 10 psig). Moreover, the feed rate to this stripper is desirably set so that the combined amount of ethylene and propylene in the stripper bottoms is less than 100 ppm and, in accordance with a preferred embodiment the feed rate to this stripper is desirably set so that the combined amount of ethylene and propylene in the stripper bottoms is less than 5 ppm.

A stream containing stripped hydrocarbons, including stripped ethylene and stripped propylene, is withdrawn from the first stripping zone 14 via an overhead line 50. As will be appreciated by those skilled in the art, the stream withdrawn in such overhead line may in addition to stripped hydrocarbons including ethylene and propylene also contain some minor amount, e.g., typically less than 1 wt. % of carbon dioxide.

The line 50 and the stream of stripped hydrocarbons and $CO_2$ contained therewithin can be sent for further processing such as is known in the art. For example, in accordance with one preferred embodiment, such stream or at least selected portions thereof can desirably be returned to the main column receiver so as to permit desired olefin recovery therefrom. Those skilled in the art and guided by the teachings herein provided will appreciate that while such return and processing may lead to the recycle of some $CO_2$, the amount of such recycle in practice will generally not be so significant as to make such processing uneconomical.

A process stream primarily containing absorption solvent and remaining carbon dioxide is withdrawn from the first stripping zone 14 via a line 52. The process stream in the line 52 is passed through a pump 54, a line 56, a lean/rich $CO_2$ stream heat exchanger 60 and a line 62 into the second stripping zone 16.

As will be appreciated by those skilled in the art and guided by the teachings herein provided, suitable second stripping zones for use in the practice of the invention may desirably be in the form of a column and contains or includes an active stripping section or portion 64 such as includes a selected number of trays or other stripping column internals such as may be desired to facilitate or otherwise help effect the desired stripping action. As shown, the point of introduction into the second stripping zone 16 of the line 62 containing absorption solvent and remaining carbon dioxide may desirably be situated above the active stripping section 64 and the point of introduction into the second stripping zone 16 of a line 66 containing a stream of a selected stripping fluid may desirably be situated below the active stripping section 64, such that the stripping fluid and the material to be treated within the second stripping zone 16 are in at least a general countercurrent flow arrangement. Moreover, such placement of the points of introduction of the stream of material to be treated and the stripping fluid, respectively, can desirably maximize the effect of any column internals and the effective contact time and residence time of the stream materials within the second stripping zone active section 64.

The second stripping zone 16 is desirably operated in a manner, including second stripping conditions, effective to strip at least a portion of the carbon dioxide from the second process stream to form a carbon dioxide overhead stream, shown as a line 70, and an absorption solvent bottoms stream, shown as a line 72, that is substantially free of carbon dioxide.

In general it is preferred to operate at as low a pressure as possible in order to most appropriately limit the temperature of the bottoms stream. In practice, suitable such stripping conditions generally include: an operating pressure such as in the range of about 103 kPag to about 138 kPag (about 15 psig to about 20 psig).

Prior to exiting the second stripping zone 16, the carbon dioxide overhead stream materials are passed through a wash zone 74 where a wash material, such as water, is introduced through a line 76 to contact the stripped materials and to desirably remove entrained absorbent solvent that may have remained therewith. The used wash material containing such removed absorption solvent is withdrawn from the second stripping zone 16 via a line 78 and can desirably be processed in a manner as is known in the art, such as to provide additional stripping vapor.

If desired and as shown, a first portion of the $CO_2$ overhead stream 70 can be returned to the first stripping zone 14 such as via the line 46 for use as a stripping fluid therein. A second or remaining portion of the $CO_2$ overhead stream 70 can form a purge stream, shown as in a line 80.

A first portion of the absorption solvent bottoms stream from the line 72 can pass through a line 82 to a reboiler 84 and through the line 66 back into the second stripping zone 16. A second portion of the absorption solvent bottoms stream from the line 72 can pass through a line 90 to the lean/rich $CO_2$ stream heat exchanger 60 and then through lines 92 and 94 to a recirculation pump 96 and then through lines 100 and 22 to be appropriately introduced into the absorption zone 12. A portion of the absorption solvent material in the line 100 can be processed via a line 102 through a filter device 104 and then back through a line 106 to form a portion of the stream of material in the line 94 introduced into the recirculation pump 96.

As will be appreciated by those skilled in the art and guided by the teachings herein provided, conventional amine system treatment processing may generally involve a tradeoff involving operating pressure. At low pressure operation, there is generally reduced or minimal coabsorption of hydrocarbon, but the required rate for solvent recycle is relatively large. In contrast, at high pressure operation, the solvent flow rate may desirably be reduced, but more hydrocarbons (in the case of the processing of the subject ethylene-rich streams, particularly ethylene and propylene) may be coabsorbed. With a subject amine treatment section such as described above, however, such coabsorbed ethylene and propylene is desirably recovered via the first stripping zone 14 such that the overall loss of light olefins due to amine treatment is minimized or avoided. Consequently, the subject amine treatment section can desirably be operated at relative higher pressures such as to reduce or minimize solvent recirculation. Thus, in accordance with a preferred embodiment, the absorption zone 14 and the amine absorber thereof are advantageously located at a high, if not highest, pressure location in the process scheme in order to minimize solvent recirculation.

The first stripping zone will generally operate most efficiently and require the least amount of $CO_2$ recirculation when operated at relatively low pressures. In the above-described embodiment, such as when the stream of hydrocarbons in the first stripper overhead line 50 is returned to the main column receiver, such as operates at about 34 kPag (5 psig), the pressure in the first stripping zone 14 generally needs to be high enough to permit the return of such off-gas stream to the main column receiver while allowing for line pressure drops, e.g., slightly greater than the main column receiver operating pressure.

The second stripping zone will generally operate at a pressure high enough to permit $CO_2$ to be desirably circulated to the lower portion of the first stripping zone stripper while allowing for line and unit pressure drops. This obviates the need to use a recycle blower in order to return $CO_2$ to the first stripping zone. Consequently, in a preferred embodiment, the second stripping zone preferably operates at a pressure greater than the operating pressure of the first stripping zone.

Thus, effective and efficient amine system processing of high olefin content (e.g., ethylene-rich) carbon dioxide-containing streams such as for the effective separation and removal of carbon dioxide therefrom while desirably permitting increased or improved olefin recovery are provided.

The treatment of ethylene-rich hydrocarbon and carbon dioxide-containing streams in the manner described above can find particular application in the production of light olefins via the catalytic cracking of a heavy hydrocarbon feedstock.

Figure 2:
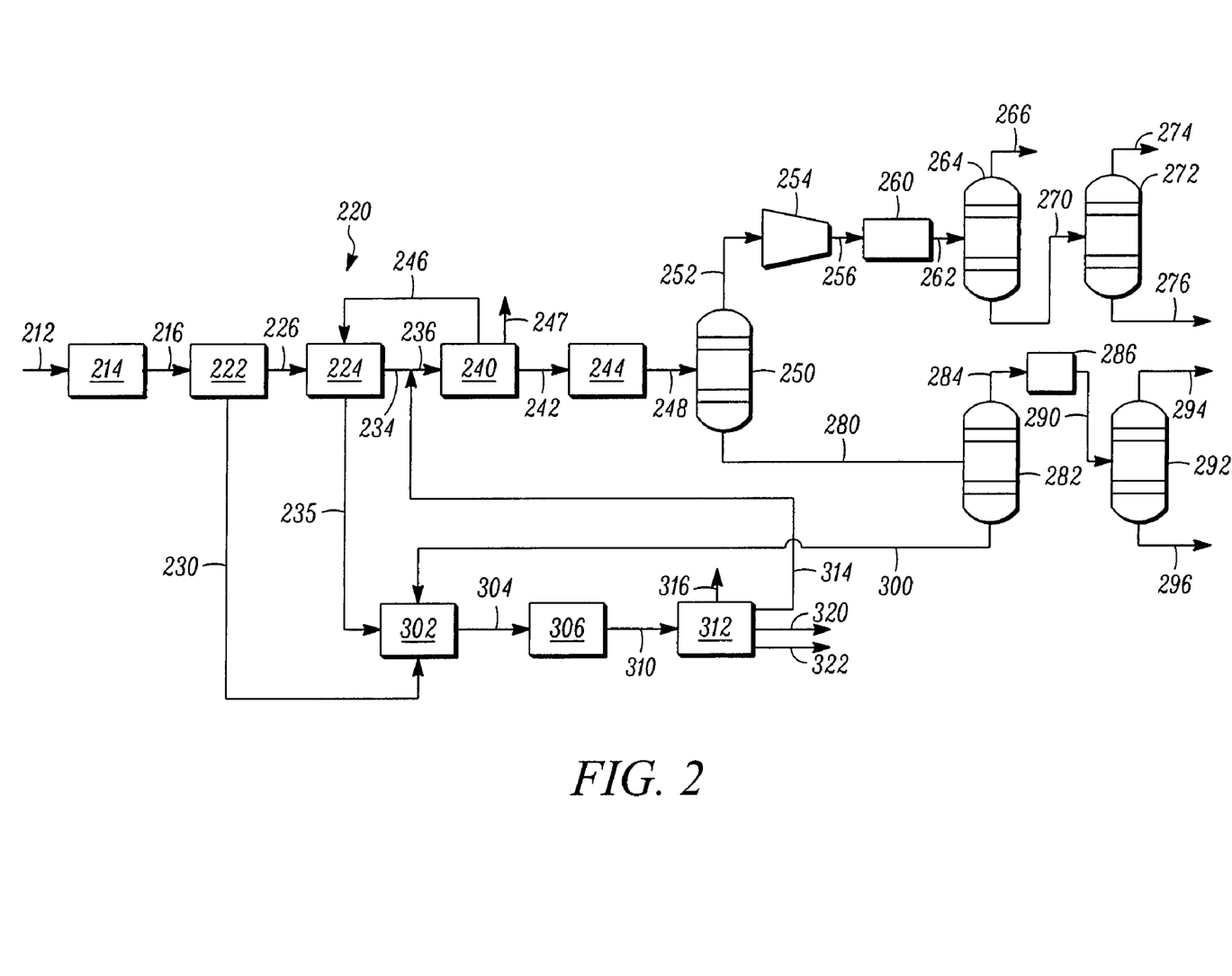
FIG. 2 is a simplified schematic diagram of a system for catalytic cracking a heavy hydrocarbon feedstock and obtaining light olefins substantially free of carbon dioxide in accordance with one preferred embodiment.

Turning to FIG. 2, there is illustrated a simplified schematic diagram of a system, generally designated by the reference numeral 210, for catalytic cracking a heavy hydrocarbon feedstock and obtaining light olefins substantially free of carbon dioxide, in accordance with one embodiment of the invention.

In the system 210, a suitable heavy hydrocarbon feedstock stream is introduced via a line 212 into a fluidized reactor zone 214 wherein the heavy hydrocarbon feedstock contacts with a hydrocarbon cracking catalyst zone to produce a hydrocarbon effluent comprising a range of hydrocarbon products, including light olefins, and a quantity of carbon dioxide.

Suitable fluidized catalytic cracking reactor zones for use in the practice of such an embodiment may, as is described in above-identified U.S. Pat. No. 6,538,169 B1 to Pittman et al., include a separator vessel, a regenerator, a blending vessel, and a vertical riser that provides a pneumatic conveyance zone in which conversion takes place. The arrangement circulates catalyst and contacts feed in a specifically described manner.

More specifically and as described therein, the catalyst typically comprises two components that may or may not be on the same matrix. The two components are circulated throughout the entire system. The first component may include any of the well-known catalysts that are used in the art of fluidized catalytic cracking, such as an active amorphous clay-type catalyst and/or a high activity, crystalline molecular sieve. Molecular sieve catalysts are preferred over amorphous catalysts because of their much-improved selectivity to desired products. Zeolites are the most commonly used molecular sieves in FCC processes. Preferably, the first catalyst component comprises a large pore zeolite, such as a Y-type zeolite, an active alumina material, a binder material, comprising either silica or alumina and an inert filler such as kaolin.

The zeolitic molecular sieves appropriate for the first catalyst component should have a large average pore size. Typically, molecular sieves with a large pore size have pores with openings of greater than 0.7 nm in effective diameter defined by greater than 10 and typically 12 membered rings. Pore Size Indices of large pores are above about 31. Suitable large pore zeolite components include synthetic zeolites such as X-type and Y-type zeolites, mordenite and faujasite. It has been found that Y zeolites with low rare earth content are preferred in the first catalyst component. Low rare earth content denotes less than or equal to about 1.0 wt-% rare earth oxide on the zeolite portion of the catalyst. Octacat™ catalyst made by W. R. Grace & Co. is a suitable low rare earth Y-zeolite catalyst.

The second catalyst component comprises a catalyst containing, medium or smaller pore zeolite catalyst exemplified by ZSM-5, ZSM-11, ZSM-12, ZSM-23, ZSM-35, ZSM-38, ZSM-48, and other similar materials. U.S. Pat. No. 3,702,886 describes ZSM-5. Other suitable medium or smaller pore zeolites include ferrierite, erionite, and ST-5, developed by Petroleos de Venezuela, S. A. The second catalyst component preferably disperses the medium or smaller pore zeolite on a matrix comprising a binder material such as silica or alumina and an inert filer material such as kaolin. The second component may also comprise some other active material such as Beta zeolite. These catalyst compositions have a crystalline zeolite content of 10-25 wt. % or more and a matrix material content of 75-90 wt. %. Catalysts containing 25 wt. % crystalline zeolite material are preferred. Catalysts with greater crystalline zeolite content may be used, provided they have satisfactory attrition resistance. Medium and smaller pore zeolites are characterized by having an effective pore opening diameter of less than or equal to 0.7 nm, rings of 10 or fewer members and a Pore Size Index of less than 31.

The total catalyst composition should contain 1-10 wt. % of a medium to small pore zeolite with greater than or equal to 1.75 wt. % being preferred. When the second catalyst component contains 25 wt. % crystalline zeolite, the composition contains 4-40 wt. % of the second catalyst component with a preferred content of greater than or equal to 7 wt. %. ZSM-5 and ST-5 type zeolites are particularly preferred since their high coke resistivity will tend to preserve active cracking sites as the catalyst composition makes multiple passes through the riser, thereby maintaining overall activity. The first catalyst component will comprise the balance of the catalyst composition. The relative proportions of the first and second components in the catalyst composition will not substantially vary throughout the FCC unit.

The high concentration of the medium or smaller pore zeolite in the second component of the catalyst composition improves selectivity to light olefins by further cracking the lighter naphtha range molecules. But at the same time, the resulting smaller concentration of the first catalyst component still exhibits sufficient activity to maintain conversion of the heavier feed molecules to a reasonably high level.

The relatively heavier feeds suitable for processing in accordance herewith include conventional FCC feedstocks or higher boiling or residual feeds. A common conventional feedstock is vacuum gas oil which is typically a hydrocarbon material prepared by vacuum fractionation of atmospheric residue and which has a broad boiling range of from 315-622° C. (600-1150° F.) and, more typically, which has a narrower boiling point range of from 343-551° C. (650-1025° F.). Heavy or residual feeds, i.e., hydrocarbon fractions boiling above 499° C. (930° F.), are also suitable. The fluidized catalytic cracking processing the invention is typically best suited for feedstocks that are heavier than naptha range hydrocarbons boiling above about 177° C. (350° F.).

The effluent or at least a selected portion thereof is passed from the fluidized reactor zone 214 through a line 216 into a hydrocarbon separation system 220, such as includes a main column section 222 and a staged compression section 224. The main column section 222 may desirably include a main column separator with an associated main column overhead high pressure receiver wherein the fluidized reactor zone effluent can be separated into desired fractions including a main column vapor stream, such as passed through a line 226, and a main column liquid stream, such as passed through a line 230.

To facilitate illustration and discussion, other fraction lines such as including a heavy gasoline stream, a light cycle oil ("LCO") stream, a heavy cycle oil ("HCO") stream and a clarified oil ("CO") stream, for example, may not here be shown nor hereinafter specifically described.

The main column vapor stream line 226 is introduced into the staged compression section 224, such as constituting a three-stage compression. The staged compression section 224 results in the formation of a high pressure separator vapor stream, such as typically primarily comprising $C_4-$ hydrocarbons and including a quantity of carbon dioxide, in a line 234. While the pressure of such high pressure vapor and, in turn, corresponding high pressure liquid, can vary, in practice such streams are typically at a pressure in the range of about 1650 kPa to about 1930 kPa (about 240 psia to about 280 psia).

The compression section 224 may also result in the formation of a stream of spill back materials largely composed of heavier hydrocarbon materials and typically in the form of a liquid. Such liquid material typically primarily comprises $C_4+$ hydrocarbons and is substantially free of carbon dioxide. Such spill back material can be passed via one or more lines 235 for further processing or treatment as later described herein.

The separator vapor stream is passed via the lines 234 and 236 and is introduced into an amine treatment section 240 such as described above, to effect $CO_2$ removal therefrom. A stream containing $C_4-$ hydrocarbons substantially free of carbon dioxide is passed through a line 242 to a drier section 244, such as in the form of an adsorbent drier. Those skilled in the art and guided by the teachings herein provided will, however, appreciate that suitable other forms of driers such as known in the art can, if desired, be used.

A stream containing stripped hydrocarbons and trace amounts of $CO_2$, such as corresponding to the overhead line 50 from the first stripping zone 14 in the above-described amine treatment system 10, is conveyed from the amine treatment section 240 via a line 246 such as back to the compression section 224 such as for further processing such as consistent with the above description.

A stream containing $CO_2$ rich purge gas, such as corresponding to the purge line 80 from the second stripping zone 16 in the above-described amine treatment system 10, is conveyed from the amine treatment section 240 via a line 247.

A stream containing dried $C_4-$ hydrocarbons substantially free of carbon dioxide is passed via a line 248 to a deethanizer 250. A suitable such deethanizer, in accordance with one preferred embodiment, generally desirably operates at a feed temperature in the range of about 54° C. (corresponding to operation with no post compression heat exchange) to about −40° C. (about 130° F. to about −40° F.) and in accordance with a preferred embodiment with a feed temperature in the range of about 17° C. to about −40° C. (about 0° F. to about −40° F.), more preferably at about −40° C. (about −40° F.); a top tray temperature in the range of about −34° C. to about −46° C. (about −30° F. to about −50° F.) and in accordance with a preferred top tray temperature of about −46° C. (about −50° F.); and with a $C_2$ recovery generally of at least 98 mol %, preferably with a $C_2$ recovery of at least 99 mol % to about 99.9 mol % and, more preferably with a $C_2$ recovery of at least 99.9 mol %.

From the deethanizer 250, a stream of $C_2-$ hydrocarbons is taken overhead via a line 252. The line 252 and the stream of materials therein contained are introduced into a compressor section 254 to form a corresponding stream of compressed materials (such as being at a pressure in the range of about 3720 kPag to about 3865 kPag (about 540 psig to about 560 psig)) that are passed through a line 256 to an acetylene conversion section or unit 260. As is known in the art, acetylene conversion sections or units are effective to convert acetylene to form ethylene. Thus, an additionally ethylene-enriched process stream is withdrawn in a line 262 from the acetylene conversion section or unit 260.

The process stream in the line 262 is introduced into a demethanizer 264. A suitable such demethanizer, in accordance with one preferred embodiment, includes a condenser (not specifically shown) that desirably operates at a temperature of no greater than about −90° C. (−130° F.), more preferably operates at a temperature in the range of about −90° C. to about −102° C., preferably about −96° C. (−130° to about −150° F., preferably at about −140° F.). In addition, a preferred demethanizer for use in the practice of the invention desirably operates with a methane to ethylene molar ratio in the bottoms of no greater than about 0.0005 and, more preferably at a methane to ethylene molar ratio in the bottoms of no greater than about 0.0003 to about 0.0002.

A stream of methane and hydrogen gas from the demethanizer 264 is taken overhead by via a line 266 such as for use as a fuel or, if desired for further processing or treatment such as to a pressure swing absorption unit (not shown) for $H_2$ recovery. A line 270 withdraws a stream of demethanized material from the demethanizer 264. The stream of demethanized material in line 270 is passed to an ethylene/ethane splitter 272. A suitable such ethane/ethylene splitter, in accordance with one preferred embodiment, includes a condenser (not specifically shown) that desirably operates at a pressure in the range of about 1930 kPag to about 2105 kPag (about 280 psig to about 305 psig), and desirably operates such that there is no more than about 0.5 vol. % ethane in the ethylene product stream, preferably less than about 0.1 vol. % ethane in the ethylene product stream and, more preferably, less than about 0.05 vol. % ethane in the ethylene product stream.

The ethylene/ethane splitter 272 forms a stream of ethylene and a stream of ethane which are passed through lines 274 and 276, respectively, such as either for product recovery or further desired processing, as is known in the art.

The deethanizer 250 also produces or forms a stream of $C_3$+ hydrocarbons such as withdrawn therefrom via a line 280. The line 280 introduces the materials passing therein into a depropanizer 282. A suitable such depropanizer, in accordance with one preferred embodiment, includes a condenser (not specifically shown) that desirably operates at a pressure in the range of about 1030 kPag to about 1175 kPag (about 150 psig to about 170 psig), with a recovery of at least about 98 mol % of the $C_3$ hydrocarbons in the overhead, more preferably with the recovery of at least in the range of 98-99.5 mol % of the $C_3$ hydrocarbons in the overhead and at least 95 mol % of the $C_4$+ hydrocarbons in the bottoms product, more preferably with the recovery of at least about 95 mol % to about 99 mol % of the $C_4$+ hydrocarbons in the bottoms product.

A stream of $C_3$ hydrocarbons is taken overhead from the depropanizer 282 via a line 284. This stream of $C_3$ hydrocarbons, in addition to propane and propylene may contain significant relative amounts or quantities of $C_3$ diolefin hydrocarbons. Thus, as shown and in accordance with one preferred embodiment, the system 210 may desirably include or contain a selective hydrogenation process unit 286 to convert such diolefinic materials to corresponding olefin materials.

The resulting stream is passed via a line 290 to a propylene/propane splitter 292. A suitable such propane/propylene splitter, in accordance with one preferred embodiment, desirably operates such that at least 98 wt. % and, preferably, at least about 99 wt. % of the propylene recovery is in the overhead stream and the propylene in the overhead stream is at least about 99.5% pure.

The propylene/propane splitter 292 forms a stream of propylene and a stream of propane which are passed through lines 294 and 296, respectively, such as either for product recovery or further desired processing, as is known in the art.

A line 300 withdraws a stream containing residual $C_4$+ hydrocarbons from the depropanizer 282. If desired and as shown, the line 300 with the stream containing residual $C_4$+ hydrocarbons from the depropanizer 282 can be introduced into a mercaptan treatment section 302, such as to effect mercaptan removal from the stream materials such as via caustic wash as is known in the art. In the illustrated embodiment, the liquid line 235 and the main column liquid stream line 230 are also introduced into the mercaptan treatment section 302 such as to effect mercaptan removal therefrom.

The resulting stream is withdrawn therefrom via a line 304. As such stream materials may contain diolefinic materials, in the illustrated embodiment, the line 304 is shown as leading into a selective hydrogenation process unit 306 to convert such diolefinic materials to corresponding olefin materials. The resulting stream containing $C_4$+ hydrocarbons is passed via a line 310 such as either for product recovery or further desired processing, as is known in the art.

While in the above-described embodiment, the line 300 containing the stream of residual $C_4$+ hydrocarbons withdrawn from the depropanizer 282 has been shown as being introduced into the mercaptan treatment section 302, those skilled in the art and guided by the teaching herein provided will appreciate that the broader practice of the invention is not necessarily so limited. For example, if desired, such as in instances or situations wherein such stream of residual $C_4$+ hydrocarbons contains little or no mercaptans, such stream of materials can be passed directly to the selective hydrogenation process unit 306.

In accordance with one preferred embodiment and as shown in FIG. 2, the resulting stream containing $C_4$+ hydrocarbons can desirably be passed via the line 310 to a further treatment and/or separation zone, generally designated by the reference numeral 312. In accordance with certain alternate preferred embodiments, such a further treatment and/or separation zone may incorporate one or more of an olefinic cracking, metathesis and alkylation processing unit alone or together with a further product separation zone, such as known in the art. For example, in an embodiment wherein the further treatment and/or separation zone 312 comprises an olefin cracking and further product separation zone, at least a portion of the $C_4$+ olefins may desirably be cracked, such as in a manner known in the art, to form a cracked olefin effluent comprising $C_2$ and $C_3$ olefins, shown as passing in a line 314, and such as can be further conveyed in the line 236 for further processing as hereinabove described.

In the illustrated embodiment, the further treatment and/or separation zone 312 also provides or results in a stream containing $C_4$ hydrocarbon materials, a stream containing $C_7$-$C_9$ hydrocarbons and a stream containing $C_{10}$+ hydrocarbons, withdrawn via lines 316, 320 and 322, respectively, and such as can be appropriately passed for further processing or product recovery, as may be desired. Those skilled in the art and guided by the teachings herein provided will appreciate that other product streams, such as known in the art, may also be formed and thus the broader practice of the invention is not necessarily limited to the specific products streams herein shown or described.

Thus processing schemes and arrangements are desirably provided for obtaining light olefins substantially free of carbon dioxide via the catalytic cracking of a heavy hydrocarbon feedstock. More particularly, processing schemes and arrangements are provided that advantageously utilize fractionation of hydrocarbon effluent products to produce or otherwise form process streams containing specifically desired ranges of hydrocarbons.

The invention illustratively disclosed herein suitably may be practiced in the absence of any element, part, step, component, or ingredient which is not specifically disclosed herein.

While in the foregoing detailed description this invention has been described in relation to certain preferred embodiments thereof, and many details have been set forth for purposes of illustration, it will be apparent to those skilled in the art that the invention is susceptible to additional embodiments and that certain of the details described herein can be varied considerably without departing from the basic principles of the invention.

What is claimed is:

1. A process for catalytically cracking a heavy hydrocarbon feedstock and obtaining light olefins substantially free of carbon dioxide, the process comprising:
   contacting a heavy hydrocarbon feedstock with a hydrocarbon cracking catalyst in a fluidized reactor zone to produce a hydrocarbon effluent comprising a range of hydrocarbon products, including light olefins, and a quantity of carbon dioxide;
   separating the hydrocarbon effluent in a hydrocarbon separation section comprising a compression section to form at least one separator liquid stream and a separator vapor stream, the at least one separator liquid stream comprising $C_4+$ hydrocarbons with less than about 100 ppm of carbon dioxide, the separator vapor stream comprising $C_4-$ hydrocarbons and at least a portion of the quantity of carbon dioxide;
   treating the separator vapor stream in an amine treatment section with an amine absorption solvent at treatment conditions effective to absorb a significant portion of the carbon dioxide from the separator vapor stream and to form a treated stream comprising $C_4-$ hydrocarbons substantially free of carbon dioxide and a first process stream comprising propylene and less than 1 wt. % of carbon dioxide;
   recycling said first process stream to said hydrocarbon separation section for further processing; and
   fractionating at least a portion of the treated stream comprising $C_4-$ hydrocarbons substantially free of carbon dioxide to at least form a first light olefin product stream comprising ethylene substantially free of carbon dioxide and a second light olefin products stream comprising propylene substantially free of carbon dioxide.

2. The process of claim 1 wherein said contacting of the heavy hydrocarbon feedstock with a hydrocarbon cracking catalyst comprises contacting the heavy hydrocarbon feedstock with a blended catalyst comprising regenerated catalyst and coked catalyst in a fluidized reactor zone at hydrocarbon cracking reaction conditions to produce a cracked stream containing hydrocarbon products including light olefins and a quantity of carbon dioxide, said catalyst having a catalyst composition including a first component comprising a large pore molecular sieve and a second component comprising a zeolite with no greater than medium pore size, said zeolite with no greater than medium pore size comprising at least 1.0 wt. % of the catalyst composition.

3. The process of claim 1 wherein said treating the separator vapor stream in an amine treatment section with an amine absorption solvent comprises:
   contacting at least a portion of the separator vapor stream in an absorber zone with the amine absorption solvent and at contact conditions effective to absorb a significant portion of the carbon dioxide from the separator vapor stream and to form a hydrocarbon-containing process stream substantially free of carbon dioxide and a carbon dioxide-rich amine absorption solvent-containing process stream;
   processing at least a portion of the carbon dioxide-rich amine absorption solvent-containing process stream in a first stripping zone at first stripping conditions effective to strip at least a portion of hydrocarbons remaining in the carbon dioxide-rich amine absorption solvent-containing process stream to form a first process stream comprising stripped hydrocarbons and a second process stream comprising carbon dioxide and amine absorption solvent; and
   processing at least a portion of the second process stream in a second stripping zone at second stripping conditions effective to strip at least a portion of the carbon dioxide from the second process stream to form a carbon dioxide purge stream and an amine stream.

4. The process of claim 1 wherein said fractionating comprises:
   separating at least a portion of the treated stream comprising $C_4-$ hydrocarbons substantially free of carbon dioxide to form a first product stream comprising $C_2-$ hydrocarbons and a second product stream comprising $C_3+$ hydrocarbons;
   separating $C_2$ hydrocarbons from the first product stream to form a process stream comprising $C_2$ hydrocarbons including a quantity of ethylene; and
   separating ethylene from at least a portion of the process stream comprising $C_2$ hydrocarbons.

5. The process of claim 4 wherein the process stream comprising $C_2$ hydrocarbons comprises a quantity of acetylene, the process additionally comprising:
   converting at least a portion of the quantity of acetylene in the process stream comprising $C_2$ hydrocarbons to form an ethylene-enriched process stream.

6. The process of claim 5 additionally comprising:
   compressing the process stream comprising $C_2$ hydrocarbons including ethylene and a quantity of acetylene prior to said step of converting of at least a portion of the quantity of acetylene.

7. The process of claim 5 wherein said separating ethylene from at least a portion of the process stream comprising $C_2$ hydrocarbons comprises:
   separating ethylene from the ethylene-enriched process stream.

8. The process of claim 7 wherein said separation of ethylene from the ethylene-enriched process stream comprises:
   demethanizing the ethylene-enriched process stream to form a first demethanizer product stream comprising primarily hydrogen and methane and a second demethanizer product stream comprising primarily $C_2$ hydrocarbons and
   splitting the second demethanizer product stream comprising primarily $C_2$ hydrocarbons in a $C_2$ splitter to form a first $C_2$ splitter product stream comprising primarily ethylene and a second $C_2$ splitter product stream comprising primarily ethane.

9. The process of claim 4 wherein said fractionating additionally comprises:
   separating $C_3$ hydrocarbons from the second product stream to form a process stream comprising $C_3$ hydrocarbons including propylene; and
   separating propylene from at least a portion of the process stream comprising $C_3$ hydrocarbons.

10. The process of claim 9 wherein said separating propylene from at least a portion of the process stream comprising $C_3$ hydrocarbons comprises:
    splitting the process stream comprising $C_3$ hydrocarbons in a $C_3$ splitter to form a first $C_3$ splitter product stream comprising primarily propylene and a second $C_3$ splitter product stream comprising primarily propane.

11. The process of claim 9 wherein the process stream comprising $C_3$ hydrocarbons comprises a quantity of $C_3$ diolefin hydrocarbons, the process additionally comprising:

hydrogenating at least a portion of the $C_3$ diolefin hydrocarbons to form additional propylene to form a propylene-enriched process stream.

12. The process of claim 11 wherein said separating propylene from at least a portion of the process stream comprising $C_3$ hydrocarbons comprises:

separating propylene from the propylene-enriched process stream.

13. The process of claim 1 wherein said fractionating additionally comprises:

separating $C_3$ hydrocarbons from the second product stream to form a process stream comprising $C_3$ hydrocarbons including propylene; and separating propylene from at least a portion of the process stream comprising $C_3$ hydrocarbons.

14. The process of claim 13 wherein said separating propylene from at least a portion of the process stream comprising $C_3$ hydrocarbons comprises:

splitting the process stream comprising $C_3$ hydrocarbons in a $C_3$ splitter to form a first $C_3$ splitter product stream comprising primarily propylene and a second $C_3$ splitter product stream comprising primarily propane.

15. The process of claim 13 wherein the process stream comprising $C_3$ hydrocarbons comprises a quantity of $C_3$ diolefin hydrocarbons, the process additionally comprising:

hydrogenating at least a portion of the $C_3$ diolefin hydrocarbons to form additional propylene to form a propylene-enriched process stream.

16. The process of claim 15 wherein said separating propylene from at least a portion of the process stream comprising $C_3$ hydrocarbons comprises:

separating propylene from the propylene-enriched process stream.

17. The process of claim 1 additionally comprising:

drying the treated stream comprising $C_4-$ hydrocarbons substantially free of carbon dioxide prior to said fractionation step.

18. A process for catalytically cracking a heavy hydrocarbon feedstock and obtaining light olefins substantially free of carbon dioxide, the process comprising:

contacting a heavy hydrocarbon feedstock with a regenerated catalyst in a fluidized reactor zone at hydrocarbon cracking reaction conditions to produce a hydrocarbon effluent stream comprising a range of hydrocarbon products including light olefins and a quantity of carbon dioxide, said catalyst having a catalyst composition including a first component comprising a large pore molecular sieve and a second component comprising a zeolite with no greater than medium pore size, said zeolite with no greater than medium pore size comprising at least 1.0 wt. % of the catalyst composition;

separating the hydrocarbon effluent in a hydrocarbon separation section to form at least one separator liquid stream and a separator high pressure vapor stream, the at least one separator liquid stream comprising $C_4+$ hydrocarbons with less than about 100 ppm of carbon dioxide, the separator high pressure vapor stream comprising $C_4-$ hydrocarbons and at least a portion of the quantity of carbon dioxide;

contacting at least a portion of the separator high pressure vapor stream in an absorber zone with an amine absorption solvent and at contact conditions effective to absorb a significant portion of the carbon dioxide from the contacted portion of the separator high pressure vapor stream and to form a hydrocarbon-containing process stream substantially free of carbon dioxide and a carbon dioxide-rich amine absorption solvent-containing process stream;

processing at least a portion of the carbon dioxide-rich amine absorption solvent-containing process stream in a first stripping zone at first stripping conditions effective to strip at least a portion of hydrocarbons remaining in the carbon dioxide-rich amine absorption solvent-containing process stream to form a first process stream comprising stripped hydrocarbons including propylene and less than 1 wt. % of carbon dioxide and a second process stream comprising carbon dioxide and amine absorption solvent;

recycling said first process stream to said hydrocarbon separation section for further processing;

processing at least a portion of the second process stream in a second stripping zone at second stripping conditions effective to strip at least a portion of the carbon dioxide from the second process stream to form a carbon dioxide purge stream and an amine stream; and fractionating at least a portion of the hydrocarbon-containing process stream substantially free of carbon dioxide to at least form a first light olefin product stream comprising ethylene substantially free of carbon dioxide and a second light olefin products stream comprising propylene substantially free of carbon dioxide.

19. The process of claim 18 wherein said fractionating comprises:

separating at least a portion of the at least a portion of the treated stream comprising $C_4-$ hydrocarbons substantially free of carbon dioxide to form a first product stream comprising $C_2-$ hydrocarbons and a second product stream comprising $C_3+$ hydrocarbons;

separating $C_2$ hydrocarbons from the first product stream to form a process stream comprising $C_2$ hydrocarbons including ethylene and a quantity of acetylene;

converting at least a portion of the quantity of acetylene in the process stream comprising $C_2$— hydrocarbons to form an ethylene-enriched process stream;

separating ethylene from the ethylene-enriched process stream;

separating $C_3$ hydrocarbons from the second product stream to form a process stream comprising $C_3$ hydrocarbons including propylene and a quantity of $C_3$ diolefin hydrocarbons;

hydrogenating at least a portion of the $C_3$ diolefin hydrocarbons to form additional propylene to form a propylene-enriched process stream; and separating propylene from the propylene-enriched process stream.

* * * * *